United States Patent [19]

Spitzer et al.

[11] 3,968,203
[45] July 6, 1976

[54] AEROSOL ASTRINGENT COMPOSITION

[75] Inventors: Joseph G. Spitzer, Mamaroneck; Lloyd Osipow, New York, both of N.Y.

[73] Assignees: Jerome G. Spitzer, Mamaroneck; Marvin Small, New York, both of N.Y. ; part interest to each

[22] Filed: Aug. 26, 1969

[21] Appl. No.: 853,626

Related U.S. Application Data

[63] Continuation of Ser. No. 492,268, Oct. 1, 1965, abandoned.

[52] U.S. Cl. .................................................. 424/47
[51] Int. Cl.² .......................................... A61K 7/38
[58] Field of Search ............................... 424/68, 47

[56] References Cited
UNITED STATES PATENTS

| | | | |
|---|---|---|---|
| 3,014,844 | 12/1961 | Thiel et al. | 424/45 |
| 3,081,223 | 3/1963 | Gunning et al. | 424/68 X |
| 3,088,874 | 5/1963 | Geary et al. | 424;167/45;82 |
| 3,088,874 | 5/1963 | Geary et al. | 167/82 |
| 3,095,355 | 6/1963 | Abramson et al. | 424/45 |
| 3,218,263 | 11/1965 | Boyle et al. | 424/45 X |
| 3,288,681 | 11/1966 | Goldberg et al. | 424/68 X |
| 3,472,928 | 10/1969 | Nirzi | 424/68 X |

FOREIGN PATENTS OR APPLICATIONS

| | | | |
|---|---|---|---|
| 941,692 | 11/1963 | United Kingdom | 424/68 |
| 987,301 | 3/1965 | United Kingdom | 424/68 |
| 1,111,867 | 5/1968 | United Kingdom | 424/68 |
| 1,167,173 | 10/1969 | United Kingdom | 424/68 |

OTHER PUBLICATIONS

Sagarin, *Cosmetics Science and Technology*, 9/1957, pp. 717–732, 819–829.
Shepherd, Aerosols, *Science and Technology*, 1963, pp. 47–79 and 347–351.
*Aerosol Age*, 4/1964, p. 42.
*Aerosol Age*, 4/1962, pp. 64 and 67.
Beard, *Drug and Cosmetic Industry*, 1/1955, vol. 76, No. 1, pp. 49 and 50.
Husted, Paper Presented at 46th Mid–Year Meeting of Chemical Specialties Manufacturers Assoc., Inc., Chicago, 8/1960.
Geary et al., Paper Presented at 47th Mid–Year Meeting of Chemical Specialties Manufacturers Assoc., 6/1961, pp. 80 to 82, & 91.
*Aerosol Age*, 8/1958, p. 37.
*Soap and Chemical Specialties*, 10/1964, pp. 105–107.
*Aerosol Age*, 6/1961, pp. 37, 83 and 84.
*Drug & Cosmetic Industry*, 12/1965.
*Aerosol Age*, 8/1961, pp. 22, 26–29, 71 and 72.
*Aerosol Age*, 4/1957, pp. 24 and 65.
The Toilet Goods Assoc., No. 37, 5/1962, pp. 19–26.
*Soap and Chemical Specialties*, 5/1956, pp. 164 and 165.
"Freon" Aerosol Report, 1956, pp. 1 to 11.
"Freon" Aerosol Report, 1969, pp. 1 to 6, and Appendix pp. 1 to 3.
Drug and Cosmetic Industry, 11/1966.
The Pharmaceutical Journal, 10/1964, pp. 390–395.
*Soap and Chemical Specialties*, 4/1959, pp. 69–73.
Drug and Cosmetic Industry, vol. 79, No. 3, pp. 328–329, 8/1956.
American Perfumes and Aromatics, vol. 75, No. 10, 10/1960, pp. 47 and 48.
Soap & Chemical Specialties, 6/1961, pp. 81–83 and 91.

*Primary Examiner*—Dale R. Ore
*Attorney, Agent, or Firm*—George B. Finnegan; John D. Foley

[57] ABSTRACT

This invention relates to a novel astringent antiperspirant aerosol system which comprises an astringent salt suspended in fine powder form in an anhydrous liquid vehicle and a propellant.

5 Claims, No Drawings

AEROSOL ASTRINGENT COMPOSITION

This is a continuation of Application Serial No. 492,268, filed Oct. 1, 1965, now abandoned.

This invention relates to a novel astringent and anti-perspirant aerosol system. More particularly, this invention relates to a novel astringent and anti-perspirant formulation which enables a liquid spray of an astringent to be dispensed in a conventional aerosol bomb. The aerosol astringent and anti-perspirant formulation of this invention consists essentially of an astringent material in a fine powder form suspended in a liquid vehicle which is essentially anhydrous; the liquid vehicle being of such nature that upon release of the contents from the container, the powder astringent is deposited on the skin in the form of a liquid suspension of the astringent powder.

Prior to the instant invention, there has not been available a truly commercially acceptable aerosol anti-perspirant and deodorant composition that could be packaged in a conventional metal aerosol bomb. In order to provide effective anti-perspirant activity, it is essential that there be present an astringent material. Water-soluble aluminum salts such as aluminum sulfate containing water of crystallization, aluminum chloride and aluminum chlorohydrate, which have attained increasing importance in the United States, have proved to be most effective anti-perspirants.

The above mentioned astringents and anti-perspirants are effective when present in aqueous solution. Hence, heretofore, it has generally been the practice in formulating anti-perspirant preparations employing such aluminum salts (e.g. creams, lotions, etc.) to include therein a sufficient amount of water to carry the required concentration of antiperspirant in solution.

Unfortunately, water-containing aerosol anti-perspirant formulations cause major problems when contained in conventional metal aerosol bombs. One of the major problems is corrosion caused by the corrosive action of the aluminum salt in solution. Another problem has been that the use of an effective concentration also tends to cause valve malfunction due to the crystallization of the salts in the valve orifice.

Attempts have been made to solve the above mentioned problems resulting from the use of aqueous solutions of aluminum salts by incorporating the aluminum salt in an aerosol package in such a manner that it is expelled and applied in the form of a powder. In practice this has not been satisfactory. Clouds of dust are expelled and because of the proximity of the underarm to the face, volumes of astringent aluminum salt are breathed by the user.

Objects and advantages of the invention are set forth in part herein and in part will be obvious herefrom, or may be learned by practice with the invention the same being realized and attained by means of the compositions, steps, methods and combinations pointed out in the appended claims.

The invention consists in the compositions, steps, methods, combinations and improvements herein shown and described.

An object of this invention is to provide improved aerosol astringent formulations which when contained in conventional metallic aerosol containers cause minimum or negligible internal container difficulties, and in particular, improved results with respect to corrosion and/or valve malfunction.

A further object of this invention is to provide an improved aerosol astringent composition which, when dispensed from a suitable container, is applied to the skin as a wet spray in the form of a liquid suspension of astringent material, said astringent material being activated to effect anti-perspirant activity by the moisture of the air and the body.

A further object of this invention is to provide an improved astringent preparation which may be applied to the skin as a wet spray of astringent which imparts thereto a feeling of lubrication and also reduces the likelihood of breathing the astringent as would be the case when a dry powder or dust of astringent material is dispensed from a container and applied to the skin.

Another object of this invention is to provide an improved astringent preparation in aerosol form which minimizes valve malfunction such as clogging and leakage.

It has been found that the objects of this invention may be realized by providing an aerosol astringent composition comprising an astringent material in fine powder form suspended in a liquid vehicle which is essentially anhydrous, the liquid vehicle containing as essential components a liquefied propellant and a non-volatile, non-hygroscopic liquid. When stored in a suitable aerosol container, the astringent material is in an inactive state because of the essentially anhydrous environment rather than in a water-solution active form. Hence, because of the inactive nature of the astringent while in the container the problem of corrosion caused by the corrosive action of the astringent when in its active state is avoided. Upon release from the container, however, the astringent is applied to the skin, as a wet spray, in the form of a liquid suspension of fine powder astringent, the astringent material exhibiting astringent and anti-perspirant properties when converted to its active form by the moisture in the air and on the body.

As indicated hereinbefore, an essential component of the liquid vehicle of the aerosol formulation of this invention is a non-volatile, non-hygroscopic liquid. Such non-volatile, non-hygroscopic liquid component serves to maintain the expelled and deposited astringent powder as a liquid, relatively dust-free spray.

Depositing the astringent on the skin in the form of a liquid spray containing the astringent powder dispensed in a non-volatile liquid affords many advantages. First of all, since a liquid rather than a dry powder is applied to the skin, the skin feels lubricated and does not feel dry and harsh, as would be the case if a powder was deposited on the skin.

Secondly, since the liquid component of the wet spray is non-volatile, the spray effectively adheres to the skin so that the astringent when in its active form can exert effective anti-perspirant activity over a desired long period of time.

Thirdly, if a non-volatile liquid were not part of the liquid vehicle for the astringent powder of the aerosol formulation, the resulting product when dispensed from the container would be a fine dust which would settle very slowly. When sprayed under the arms, it would be quite difficult to avoid breathing the dust, with the result that the astringent would enter the lungs. When the liquid vehicle contains a non-volatile liquid, as is the case in the instant invention, the droplets of the resulting spray are relatively large and settle rapidly. Consequently, the likelihood of breathing the astringent is very much reduced.

A further advantage in the use of a non-volatile non-hygroscopic liquid as a component of our aerosol formulation, is that it, in combination with the other liquefied components, maintains the anti-perspirant aluminum salts in an insoluble, non-ionizing condition, as a consequence of which the salts are non-corrosive to metals.

From the above discussion, it becomes readily apparent that if one is to realize the desired objectives, a non-volatile, non-hygroscopic liquid must be included as an essential component for mixture with the liquefied propellant in providing the desired liquid vehicle for the astringent powder. The use of a volatile component, e.g. alcohol, instead of a non-volatile component would not give suitable results. First, since alcohol is of a volatile nature, it would evaporate fairly quickly to leave a powder deposited on the skin, the disadvantages of which having been discussed hereinbefore in detail. Second, it would be much more difficult to compound with alcohol and keep it anhydrous than with a non-volatile, non-hygroscopic liquid used in accordance with the instant invention. Even if only a small amount of water were introduced, as would be quite probable if alcohol were employed, corrosion would result. Third, by using a volatile liquid, such as alcohol, a small residue remains on the actuator. The liquid evaporates leaving a powdered dry aluminum salt on the actuator. This picks up moisture from the atmosphere which dissolves the aluminum salt, if some moisture evaporates or the temperature drops, large crystals form which clog the actuator. These problems are avoided by the use of a non-volatile, non-hygroscopic liquid.

The principles of this invention are applicable to any astringent material which, in dry powder form is in an inactive state, but, which, in the presence of moisture, is converted to an active state. Examples of astringents of the aforementioned type are the astringent salts of multi-valent cations such, for example, as the divalent astringent salts exemplified by zinc chloride, zinc sulfate and zinc sulfocarbolate, the trivalent astringent salts such as aluminum sulfate, aluminum chloride, aluminum sulfocarbolate, aluminum chlorohydrate, ferric chloride; and tetra valent astringent salts such as zirconium tetrachloride, zirconium sulfate. The preferred anti-perspirant agent of this invention are the above mentioned astringent aluminum salts.

Suitable non-volatile, non-hygroscopic liquid for use in combining with the liquified propellant in providing the desired liquid vehicle are essentially non-polar organic liquids having: (a) a vapor pressure less than about 25 mm of mercury at 70°F; (b) a boiling point at atmospheric pressure not lower than 250°F; (c) a dielectric constant not greater than 10, and preferably less than 5; (d) a specific gravity between 0.7 and 1.6 and preferably between 0.7 and 1.2; and (e) a water insolubility such that it will not dissolve more than about 5% of water at 70°F. Examples of such materials are hydrophilic oils such as hydrocarbon oils exemplified by tetradecane; organic esters such as isopropyl myristate and glyceryl trioleate; alcohols such as lauryl alcohol; carboxylic acids such as oleic acid; and, silicone oils such as the dimethylpolysiloxanes.

Any conventional propellant, or mixture of propellants may be used that has the desired vapor pressure at atmospheric temperature to effect dispensing of the contents of the container but which pressure is not unduly excessive so as to cause excessive dusting when the astringent formulation is sprayed against the skin. Generally, the vapor pressure is in the range of 15 to 75 p.s.i.g. at 70°F., and preferably 20 to 50 p.s.i.g. Examples of materials that may be used as a propellant component, either alone or in admixture, are trichlorofluoromethane (Freon 11), dichlorodifluoromethane (Freon 12), tetrafluorodichloroethane (Freon 114), pentafluoromonochloroethane (Freon 115), cyclic hexafluorodichlorobutane (Freon C 316), octafluoropropane (Freon 218), cyclic octafluoro-butane (Freon C 318), propane, butane, pentane and isobutane.

Also, the propellant should not react with the astringent material or the non-volatile, non-hygroscopic liquid or any other consitutent of the aerosol formulation to create difficulties while the aerosol formulation is contained in the can or deleteriously affect their desired activities when applied to the skin.

The astringent should be in an amount sufficient to impart the desired anti-perspirant activity when activated by the moisture in the air but should not be in too great an amount to cause excessive dusting when sprayed against the skin. In general, the astringent is in an amount from .2 to 10% and preferably .5 to 5% by weight of the total composition, and in an amount from .01 to 1.0 part by weight and preferably .05 to .3 part per part of the non-volatile, non-hygroscopic liquid. Also, the astringent should have a particle size sufficiently small to minimize valve malfunction. In general, the astringent powder has a particle size in the range of 1 to 100 microns, and preferably less thant 50 microns.

The non-volatile, non-hygroscopic liquid should be in an amount sufficient whereby the astringent is deposited on the skin in the form of a wet spray but should not be in too high an amount wherein it would interfere with the anti-perspirant action of the astringent as well as causing the wet spray deposited on the skin to be of too oily a nature. In general, the non-volatile non-hygroscopic liquid is in an amount from 2 to 50 % by weight of the total composition, preferably 5 to 25% by weight.

As indicated hereinbefore, the propellant should be in an amount to provide the desired vapor pressure for dispensing the desired contents from the container without causing excessive dusting when the wet spray containing the dispensed astringent is applied against the skin. In general, the propellant is in an amount from 50 to 98% by weight of the total composition, preferably 75 to 95% weight.

It has been found desirable to incorporate in the aerosol compositions of this invention certain materials which have grease-like imparting properties to the non-volatile, non-hygroscopic liquid and greatly aid in preventing malfunction of the aerosol valve. These materials are characterized by the fact that they prevent compacting of the anti-perspirant powder in the completed composition and they also act as thickening or jelling agents for the non-volatile, non-hygroscopic liquid. Examples of such materials are hydrophobic treated clays that swell in organic solvents, e.g. hydrophobic bentonite, e.g. Bentone 34, a reaction product of bentonite and dimethyl distearyl ammonium chloride, the latter constituting one third of the Bentone compound; colloidal silicas, e.g. Cab-O-Sil M-5, a submicroscopic particulate silica prepared in a hot gas environment (1100°C) by the vapor phase hydrolysis of a silicon compound; grease forming soaps such as aluminum stearate. Agents of the aforedescribed type are of colloidal dimensions and in general have a particle size below 5 microns. In general, these agents are in an amount up to 1% by weight of the total composition and preferably 0.05 to 1% by weight.

As is the usual practice for astringent cosmetic compositions, there may be included small amounts of a perfume. In general, the perfume is in an amount up to 2% by weight of the total composition, and preferably 0.05 to 2% by weight.

Also, if so desired, there may be included in our aerosol formulation, a small amount of an anti-bacterial agent, e.g. hexachlorophene, to impart thereto deodorant characteristics. In general, the anti-bacterial agent is in an amount up to 0.5% by weight of the total composition, and preferably 0.02 to 0.2% by weight.

In order to illustrate the invention more specifically, the following working examples are now given:

Example 1

| | Parts by Weight |
|---|---|
| Aluminum chlorohydrate impalpable powder | 2.0 |
| Hexachlorophene | 0.1 |
| Bentone No. 34 | 0.3 |
| Isopropyl myristate | 6.0 |
| Trifluorotrichloroethane | 12.6 |
| Tetrafluorodichloroethane | 65.0 |
| Difluorodichloromethane | 14.0 |

Example 2

| | |
|---|---|
| Aluminum chlorohydrate impalpable powder | 3.0 |
| 3,5,4' Tribromosalicylanilide | 0.1 |
| Cab-O-Sil, M-5 | 0.6 |
| Butyl stearate | 10.0 |
| Tetrafluorodichloroethane | 66.3 |
| Difluorodichloromethane | 20.0 |

Example 3

| | |
|---|---|
| Aluminum sulfocarbolate (less than 50 microns diameter) | 4.0 |
| Hexaclorophene | 0.2 |
| Cab-O-Sil, M-5 | 0.5 |
| Mineral Oil | 5.0 |
| Hexane | 10.0 |
| Isobutane | 80.3 |

Example 4

| | |
|---|---|
| Aluminum sulfate (less than 50 microns diameter) | 1.0 |
| 3,5,4' Tribromosalicylanilide | 0.2 |
| Bentone No. 34 | 0.4 |
| Isopropyl palmitate | 10.0 |
| Fluorotrichloromethane | 63.4 |
| Difluorodichloromethane | 25.0 |

Example 5

| | |
|---|---|
| Aluminum chlorohydrate impalpable powder | 2.0 |
| Hexachlorophene | 0.2 |
| Bentone No. 34 | 0.3 |
| Oleyl Alcohol | 5.0 |
| Hexane | 10.0 |
| Tetrafluorodichloroethane | 52.5 |
| Difluorodichloromethane | 30.0 |

Example 6

| | |
|---|---|
| Aluminum chlorohydrate impalpable powder | 2.0 |
| Hexachlorophene | 0.1 |
| Isopropyl myristate | 6.0 |
| Trifluorotrichloroethane | 12.9 |
| Tetrafluorodichloroethane | 65.0 |
| Difluorodichloromethane | 14.0 |

The invention in its broader aspects is not limited to the specific compositions, steps, methods, combinations and improvements described, but departures may be made therefrom within the scope of the accompanying claims without departing from the principles of the invention and without sacrificing its chief advantages.

What is claimed is:

1. A package for containing and dispensing an astringent and anti-perspirant agent including in combination a. a pressure-tight metallic container having a valve-controlled opening and a valve for dispensing liquid in aerosol form, and
   b. a composition in said container consisting essentially of
   c. an aluminum chlorohydrate astringent in fine powder form of about 1 to 100 microns, said astringent being in an inactive state while dry but being corrosive to the metal of said container and having anti-perspirant properties in the presence of moisture, and
   d. an essentially anhydrous liquid vehicle serving to maintain the composition in liquid form and free from moisture while in said container, said astringent powder being suspended and dispersed in said liquid within the container,
   e. said liquid vehicle consisting essentially of
      1. A liquified propellant which is gaseous at room temperature and atmospheric pressure and non-reactive with the other components present in said package and
      2. a non-volatile, non-hygroscopic liquid, said non-hygroscopic liquid being a non-polar, organic liquid having (a) a vapor pressure less than about 24 mm of mercury at 70°F.; (b) a boiling point at atmospheric pressure not lower than 250°F.; (c) a dielectric constant not greater than 10; (d) a specific gravity between 0.7 and 1.6; and (e) a water insolubility such that it will not dissolve more than about 5% of water at 70°F.;
   f. said astringent powder and non-volatile, non-hygroscopic liquid being dispensed together from the container in the form of a liquid suspension upon release of the valve and volatilization of the propellant so as to be applied to the skin in the form of a liquid suspension of the astringent powder
   g. the astringent being in an amount from 0.2 – 10% by weight of the total composition, the non-volatile, non-hygroscopic liquid being in an amount from 2 to 50% by weight of the total composition and the propellant being in an amount from 50 to 98% by weight of the total composition, the relative amounts of astringent and non-volatile, non-hygroscopic liquid being in an amount from 0.01 to 1 part by weight of astringent per part by weight of the non-volatile, non-hygroscopic liquid such that the product that is applied to the skin is in the form of a liquid suspension of the astringent powder.

2. A package according to claim 1 wherein the astringent is in an amount from 0.5 to 5% by weight of the total composition and the non-volatile, non-hygroscopic liquid is in an amount from 5 to 25% by weight.

3. A package according to claim 1 wherein the astringent is in an amount of 2.0% by weight and the non-volatile, non-hygroscopic liquid is isopropyl myristate in an amount of 6.0% by weight.

4. A package according to claim 1 wherein the astringent is in an amount from 0.05 to 0.3 part by weight per part of the non-volatile, non-hygroscopic liquid.

5. A package according to claim 1 wherein the aerosol astringent and anti-perspirant composition contains an agent having grease-imparting properties with respect to the non-volatile, non-hygroscopic liquid, said grease-imparting agent selected from the group consisting of bentonite, silica and aluminum stearate.

* * * * *